(12) United States Patent
Yang et al.

(10) Patent No.: US 8,465,582 B2
(45) Date of Patent: Jun. 18, 2013

(54) PROCESS FOR PRODUCING INORGANIC INTERCONNECTED 3D OPEN CELL BONE SUBSTITUTES

(75) Inventors: Jen-Chang Yang, Taipei (TW); Sheng-Yang Lee, Taipei (TW); Tsuimin Tsai, Taipei (TW); Hong-Da Wu, Taipei (TW); Hsin-Tai Hu, Taipei (TW); Yan-Cheng Yang, Taipei (TW); Chen-Feng Ma, Taipei (TW)

(73) Assignee: Taipei Medical University, Taipei (TW)

( * ) Notice: Subject to any disclaimer, the term of this patent is extended or adjusted under 35 U.S.C. 154(b) by 347 days.

(21) Appl. No.: 12/725,163

(22) Filed: Mar. 16, 2010

(65) Prior Publication Data

US 2011/0229547 A1  Sep. 22, 2011

(51) Int. Cl.
*A61L 27/00* (2006.01)
(52) U.S. Cl.
USPC ............ 106/162.2; 521/50; 521/65; 424/423
(58) Field of Classification Search
None
See application file for complete search history.

(56) References Cited

U.S. PATENT DOCUMENTS

| | | |
|---|---|---|
| 6,905,516 B1 | 6/2005 | Lemaitre et al. |
| 2004/0010048 A1* | 1/2004 | Evans et al. ............... 521/50 |
| 2005/0119746 A1* | 6/2005 | Lidgren ............... 623/17.11 |
| 2006/0198939 A1 | 9/2006 | Smith et al. |
| 2007/0218098 A1* | 9/2007 | Reif et al. ............... 424/423 |
| 2008/0069852 A1 | 3/2008 | Shimp et al. |
| 2010/0092563 A1* | 4/2010 | Raffaele et al. ......... 424/489 |

FOREIGN PATENT DOCUMENTS

| WO | WO/2004/098457 | 11/2004 |
|---|---|---|
| WO | WO/2006/099332 | 9/2006 |

* cited by examiner

*Primary Examiner* — Melvin C Mayes
*Assistant Examiner* — Colette Nguyen
(74) *Attorney, Agent, or Firm* — WPAT, P.C.; Anthony King

(57) ABSTRACT

The present invention relates to a process of using a heat responsive mixture to produce inorganic interconnected 3D open-cell bone substitutes which can be applied in the orthopedic or dental field for treatment of bone damage. The invention provides a simple and easily-controlled process of preparing porous inorganic bone substitute materials.

16 Claims, 7 Drawing Sheets

PROCESS FOR PRODUCING INORGANIC INTERCONNECTED 3D OPEN CELL BONE SUBSTITUTES

FIELD OF THE INVENTION

This invention pertains to a method of using a heat responsive mixture to produce an inorganic interconnected 3D open-cell bone substitute applied in orthopedic and dental field. In particular, the heat responsive mixture used in the method of the invention comprises polyelectrolytic complexes and biomedical ceramic powders.

BACKGROUND OF THE INVENTION

The bony defects surgically created from tumor excision or skeletal trauma claim more than 0.5 million bone-grafting procedures in the United States annually. Autograft (bone taken from one part of the body and transferred to another part of the same individual) and allograft (bone taken from foreign body and transferred to a different individual) transplanted tissues and synthetic biomaterials usually are implanted for enhancing bone regeneration. Although tissue transplants usually have better efficacy, restrictions of inadequate sources of autograft as well as disease transfer risks limit the relevant applications. The biodegradable bone grafts in bone tissue engineering serve as temporary void fillers that can gradually be degraded and replaced by the regenerated bone tissues. Synthetic bone graft materials are preferred due to their biocompatibility, osteoconduction, and little risk of disease transmission. Typical ceramic bone graft materials such as hydroxyapatite (HA, $Ca_{10}(PO_4)_6(OH)_2$), β-tricalcium phosphate (β-TCP, $β-Ca_3(PO_4)_2$) and calcium sulfate (CS, $CaSO_4$), can be presented in different product forms such as powder, granule, pellet, putty, or block to apply to various bone damage conditions. However, these materials are mostly available in particulate or solid bulk without desired porous structure for cells and blood vessels ingrowth. Thus, the use of such materials in orthopedic and dental applications has been limited.

The porous structures of the scaffolds are especially important in tissue engineering for cells attachment and cells ingrowth to support osteocyte proliferation and differentiation. The pore size of the scaffold structure is crucial for osteoconduction. If the pore size is less than 100 µm, the bone tissue may accumulate on the graft surface only. After the implantation, the bone graft should be gradually degraded and replaced by the recipient's own bones. Pores can be categorized as either open-cell or closed-cell. The connectivity of three-dimensional pores is open-cell type which is designed to mimic the in vivo environment for enhancing the blood vessel ingrowth into the defect area.

At present, many fabrication methods for bone grafts have been developed and summarized in Table 1. Most of the commercial bone grafts are granular type. There is certain type of 3D open-cell bone grafts available. They are either fabricated by series tedious procedures or derived from naturally occurring materials like animal bones or marine (sea coral) life. Naturally occurring materials have the fixed composition such as hydroxyapatite or calcium carbonate; the degradation time of hydroxyapatite is too long, while the degradation of calcium carbonate is too short. Thus, they cannot provide suitable degradation time to meet all the requirements for various clinical applications.

TABLE 1

| Product name (producer, factory) | Composition (content) | Comments (phase) |
|---|---|---|
| Healos (Depuy Spine) | | Sponge |
| ProOsteon (Interpore Int., USA) Previous name: Replam Hydroxyapatite-Porites or RHAP | | Particulate or block brittle. Radiopaore size 190-230 µm) 500: Porites Gonipora (large pores) R: Resorbcity impedes assessment of healing. Slow resorption R-form |
| Collagraft (Zimmer Inc, USA) | HA coated 70% Type I bovine collagen | Granules and strips require augmentation with aspirated marrow |
| MBCP (Biomatlante) | Replaniform coralline macroporous HA 200: Porites (pable | Granules, rectangular sticks, cylinders or wedges |
| Triosite (Zimmer Europe Ltd, UK) | 60% HA, 40% TCP | Also called MBCP (macroporous biphasic calcium phosphate) or BCP |
| BCP (Bioland) | 60% HA, 40% TCP | |
| Ostilit (Stryker Howmedica Osteonics, UK) | 20% HA, 80% TCP, without macroporous | Granules and blocks for nonstructural grafts |
| BoneSave (Stryker Howmedica Osteonics, UK) | 20% HA, 80% TCP, pore size: 400-600 µm | Granules, stronger than Ostilit, for use as a void filler and in grafting |
| Cerasorb ORTHO (curasan) | Pure phase β-TCP, micropores: <80 µm | Granular size being 500-1,000 µm or 1,000-2,000 µm |
| Vitoss ™ Scaffold (curasan) | β-TCP, micropores: <1-1000 µm | Morsel (1-4 mm sizes) and blocks (9 × 23 mm cylinder) |
| Conduit ™ TCP Granules (DePuy Spine) | >99% (β-TCP) $Ca_3(PO_4)_2$, pore: 1-600 µm | Irregular shaped granules having an average diameter between 1.5 and 3 mm |
| Cellplex ™ TCP synthetic cancellous bone (Wright) | Porous calcium phosphate made from TCP, pore size: 100-400 µm | |
| Ceros 82 | β-TCP, porosity varies to adjust resorption between 6 and 12 months | Lower compressive strength than Ceros 80 |

TABLE 1-continued

| Product name (producer, factory) | Composition (content) | Comments (phase) |
|---|---|---|
| Synthes (USA) chronOS ™ (Synthes) | β-TCP pore size: 100-500 μm | Granules, blocks, wedge and cylinders |
| Calciresorb (Ceraver Osteal, France) | Porous TCP | Periodontal applications |
| Synthograf (Milter, USA) | Small size and dense TCP | Periodontal applications |
| Augmen (Milter, USA) | Large size and dense TCP | Periodontal applications |
| Skelite ™ (Millenium Biologix) | Multiphase, porous calcium phosphate | Granules and blocks |
| Norian Skeletal Repair System (SRS) | Self-setting calcium phosphate cement | Injectable cement, augmentation of fracture |

The prior art of different methods to form artificial porous bone grafts can be divided into several categories:

1. Dissolving and Washing

WO 20061099332A2 discloses a method of producing porous artificial composite. The method comprises using salt grains as a porogen, mixing them with calcium phosphate materials, shaping the mixture by pressing, sintering, and then dissolving the salts to form pores structure. However, this process has the disadvantage that the steps are complicated. In addition, most pores formed in the process are closed and lack of connectivity. Also, the dissolving step after sintering cannot effectively wash out the salt grains that are left inside.

2. Gasification

WO 04/098457A1 provides a method comprising using organic particles as a porogen. The method comprises the steps of mixing the pore formation agent and ceramic powder, shaping the mixture by pressing, and then sintering. The closed-cell type pores are formed as spaces left by the gasification of the organic compounds during sintering. Although pore formation agents are effective in the formation of a porous structure, the mechanical strength of the resulting product is inadequate.

3. Polyurethanes (PU) Sponge with High Porosity as a Mold

US 20060198939 provides a production method for porous open-cell ceramic composites coated with a biodegradable polymer for use as a bone substitute. This reference uses a highly porous polyurethane (PU) sponge as a template. The PU sponge is immersed into calcium phosphate slurry several times to ensure the pore structure of the PU is covered by calcium phosphate. After carefully drying, the PU sponge is removed by gasifying during sintering procedure at a high temperature. A calcium phosphate substrate with open-cell pores is obtained. However, the mechanical strength of the acquired substrate is inadequate. For this reason, the substrate is need further procedure of soaking in a polycaprolactone (PCL) solution and then dried in room temperature to enhance its mechanical property by PCL coating.

4. Foaming

US 20070218098 relates to a foaming method of produced porous calcium phosphate. The pore structure is foamed by the $CO_2$ which is produced by heating ammonium carbonate. Besides, US 20080069852 provides another foaming method by using a supercritical fluid. However, the foaming process is usually unstable and the resulted pore size is difficult to control.

5. Computer-Assisted Design and Manufacture Method

U.S. Pat. No. 6,905,516 mentions a special mold method that is designed and created by use of a computer program. The calcium phosphate slurry is infused into the mold. The structure is solidified to form hydroxyapatite and then porous structure is formed after de-molding. Interconnected pores can be generated by this method. However, the design equipment is usually expensive and the process is time-consuming.

In spite of various improvements to the processes, preparation of porous 3D open-cell bone substitutes remains significantly complex. There is a compelling need to develop a more rapid, simple, inexpensive, and reliable method of preparing bone substitutes with the required interconnective porous structures and mechanical properties.

SUMMARY OF THE INVENTION

The invention provides a method of using a heat responsive mixture to form an inorganic interconnected 3D open-pore bone substitute, wherein the heat responsive mixture comprises one or more polyelectrolytic complexes and one or more biomedical ceramic powders, comprising heating the mixture at a temperature ranging from 25° C. to 100° C., further heating the resulting mixture to remove water and polyelectrolytic complexes contained therein and then cooling the mixture, resulting in an inorganic interconnected 3D open-pore bone substitute.

DETAILED DESCRIPTION OF THE INVENTION

Figure 1:
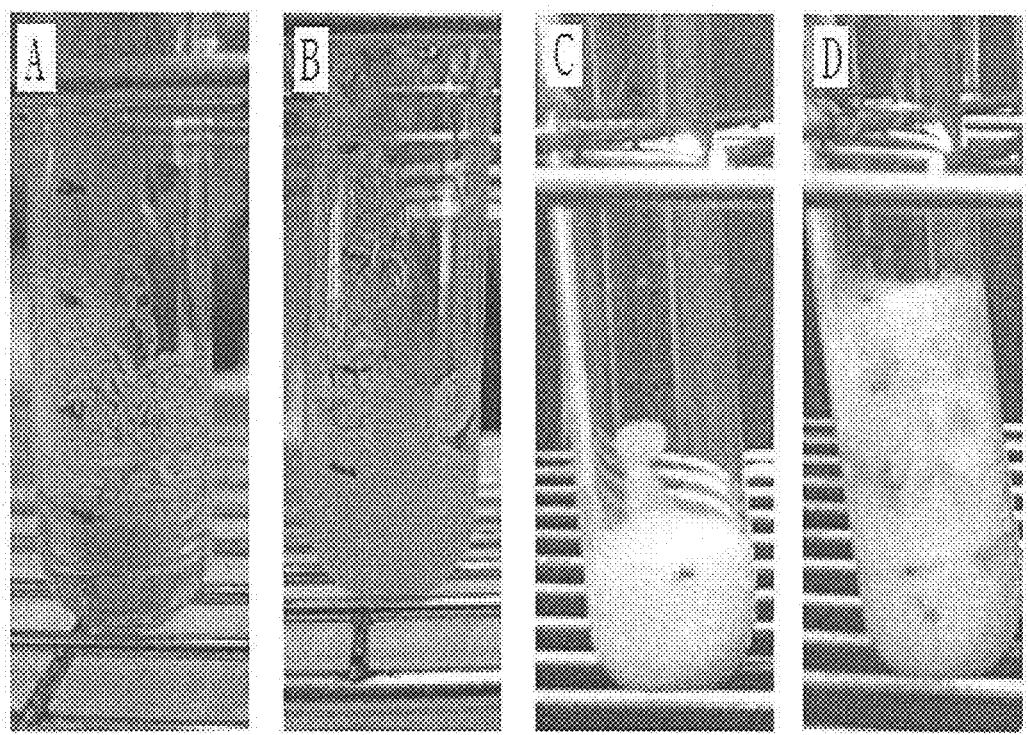
FIG. 1 shows the comparison of the volume change between a chitosan/HPMC polyelectrolytic complex and a heat-responsive mixture of chitosan/HPMC polyelectrolytic complexes and biomedical ceramic powders (HA:β-TCP=1: 9). (A) polyelectrolytic complex at 25° C.; (B) polyelectrolytic complex at 75° C.; (C) the heat-responsive mixture at 25° C.; and (D) the heat-responsive mixture at 75° C.

The present invention combines a polyelectrolytic complex and a biomedical ceramic material to form a heat-responsive mixture and, after heating the mixture, a 3D open-cell bone substitute can be generated. The 3D open-pore bone substitute can be applied in the orthopedic or dental field for treatment of bone damage. The heat-responsive mixture of the invention will, after heating, form an inorganic structure with interconnected 3D open-pore bone substitute resulting from volume expansion, water evaporation, and polyelectrolytic complex gasification. The pore size of the resulting bone substitute can be controlled by applying different heating rates. Inorganic interconnected 3D open-pore bone substitutes can be easily produced by heating the heat-responsive mixture of the invention. This process is simple and easily-controlled.

The present invention provides a method of using a heat responsive mixture to form an inorganic interconnected 3D open-pore bone substitute, wherein the heat responsive mixture comprises one or more polyelectrolytic complexes and one or more biomedical ceramic powders, comprising heating the mixture at a temperature ranging from 25° C. to 100° C., further heating the resulting mixture to remove water and polyelectrolytic complexes contained therein, and then cooling the mixture, resulting in an inorganic interconnected 3D open-pore bone substitute.

The polyelectrolytic complex of the invention is created by ion cross-linking of one or more positive charge polyelectrolyte and one or more negative charge polyelectrolyte. The oppositely-charged polymers attract one another and irreversibly bind together.

According to the present invention, the "polyelectrolyte" refers to a soluble polymer whose repeating units bear an electrolyte group. These groups will dissociate in aqueous solutions, thereby charging the polymers. The positive charge polyelectrolyte is a polyelectrolyte possessing net positive charge and the negative charge polyelectrolyte is a polyelectrolyte possessing net negative charge.

According to preferred embodiments of the present invention, the positive charge polyelectrolyte may be selected from the group consisting of polyarginine, polyornithine, DEAE dextran, polybrene, chitosan, polylysine, amino-cellulose, polyethyleneimine resin and mixture thereof.

According to preferred embodiments of the present invention, the negative charge polyelectrolyte may be selected from the group consisting of acetylcellulose, γ-polyglutamate (γ-PGA), hydroxypropyl methyl cellulose (HPMC), carboxy methyl cellulose (CMC), sodium polyphosphate, hyaluronan acid, sodium alginate and mixture thereof.

According to the present invention, the biomedical ceramic powders may be calcium phosphate based ceramic powders, calcium sulfate based ceramic powders, oxide based ceramic powders, nitride based ceramic powders, carbide based ceramic powders, alumina-dispersed zirconia or titania-dispersed alumina. Preferably, the ceramic material may be calcium phosphate, calcium sulfate, zirconia based material or mixture thereof. In one embodiment, the calcium phosphate based ceramic powder may be selected from the group consisting of hydroxyapatite (HA), β-tricalcium phosphate (β-TCP), amorphous calcium phosphate (ACP) and mixture thereof.

In another embodiment, the calcium sulfate based ceramic powder may be selected from the group consisting of calcium sulfate dihydrate, calcium sulfate hemihydrate, and calcium sulfate anhydrate.

In another embodiment, the oxide ceramic based powder may be selected from the group consisting of alumina, zirconia and titania.

In another embodiment, the nitride based ceramic powder is selected from the group consisting of silicon nitride, titanium nitride and aluminum nitride.

In another embodiment, the carbide based ceramic powder is silicon carbide.

According to the invention, the weight percent (dry weight of polyelectrolyte complex or biomedical ceramic material/wet weight of the heat-responsive mixture) of a polyelectrolyte complex and a biomedical ceramic material ranges from 2% to 40% and 10% to 75%, respectively, and the balance is water. Preferably, the weight percents of the polyelectrolyte complex are 2% to 40%, 2% to 30%, and 2% to 20%. The weight percents of the biomedical ceramic material are 10% to 75%, 20% to 75%, 30% to 75%, 40% to 75%, 50% to 75% and 60% to 75%. More preferably, the weight percent of the polyelectrolyte complex is 2% to 20% and that of the biomedical ceramic material is 15% to 50%.

According to the invention, the porous structure is affected by the concentration of the positive and negative charge polyelectrolyte.

According to the invention, the temperature for heating the responsive mixture ranges from 25° C. to 100° C. Persons skilled in the art can select an appropriate temperature depending on species of polyelectrolytic complexes. Preferably, the heating temperature ranges from 38° C. to 100° C., 55° C. to 100° C., 55° C. to 85° C., 55° C. to 80° C. or 55° C. to 75° C. More preferably, the heating temperature ranges from 55° C. to 100° C., 55° C. to 85° C., 55° C. to 80° C. or 55° C. to 75° C. After heating the heat responsive mixture of the invention, the mixture will expand and form a 3D open-pore structure.

The expanded mixture is further heated for drying, so that the water contained therein evaporates and an interconnected 3D open-pore bone substitute is formed. According to one embodiment of the invention, the heating can be performed by high temperature heating or sintering. In another embodiment, the heating can be completed in one or more stages.

In one embodiment, the temperature used in the further heating step is from 85° C. to 1500° C. Preferably, the temperature is selected from one or more of the following temperature ranges: 85° C. to 300° C., 100° C. to 250° C., 100° C. to 200° C., or 100° C. to 150° C., 300° C. to 1400° C., 300° C. to 1300° C., 300° C. to 1200° C., 300° C. to 1150° C., 300° C. to 1100° C., 300° C. to 1000° C., 500° C. to 1400° C., 500° C. to 1300° C. and 500° C. to 1200° C., depending on the selected heating stage(s). More preferably, the more preferred ranges are 100° C. to 250° C., 100° C. to 200° C., or 100° C. to 150° C., 300° C. to 1150° C. and 300° C. to 1300° C.

In another embodiment, the heating rate is 0.1 to 20° C./min, 0.3 to 15° C./min, 0.3 to 10° C./min, 0.3 to 5° C./min, 0.3 to 3° C./min or 0.3 to 2° C./min. The more preferred heating rates are 1.67° C./min, 0.63° C./min and 0.42° C./min.

In another embodiment, after raising the temperature, the method further comprises a temperature-holding session for 0.25 to 10 hours; the preferred temperature-holding session is 1 to 8 hours, 1 to 6 hours, 2 to 8 hours, 2 to 6 hours, 3 to 8 hours and 3 to 6 hours; 0.25 to 4 hours; 0.5 to 3 hours; 0.5 to 2 or 0.5 to 1 hours. The preferred temperature-holding session is 1 hour.

In another embodiment, the temperature from 300° C. to 1,500° C. is customarily used for sintering. The preferred ranges of sintering temperature are 300° C. to 1400° C., 300° C. to 1300° C., 300° C. to 1200° C., 300° C. to 1150° C., 300° C. to 1100° C., 300° C. to 1000° C., 500° C. to 1400° C., 500° C. to 1300° C. and 500° C. to 1200° C. The more preferred ranges are 300° C. to 1150° C. and 300° C. to 1300° C. The range of heating rate for the sintering is 0.1 to 20° C./min. The preferred heating rates for the sintering are 0.5 to 15° C./min, 0.5 to 10° C./min, 0.5 to 5° C./min, 1 to 15° C./min, 1 to 10° C./min, 1 to 5° C./min, 3 to 15° C./min, 3 to 10° C./min and 3 to 5° C./min. The more preferred range is 3.5° C./min. The sintering step comprises a temperature-holding session for 1 to 10 hours; the preferred temperature-holding session is 1 to 8 hours, 1 to 6 hours, 2 to 8 hours, 2 to 6 hours, 3 to 8 hours and 3 to 6 hours. The preferred session is 5 hours.

According to the invention, the pore size of the 3D open-pore bone substitutes may be controlled by the heating rate. The pore size increases inversely with the heating rate.

According to a further aspect of the present invention, the bone substitute material formed by the invention has a macro-pore size range of 0.05 to 5 millimeters, 0.05 to 3 millimeters, 0.05 to 2 millimeters, 0.05 to 1 millimeters, 0.1 to 5 millimeters, 0.1 to 3 millimeters or 0.3 to 0.5 millimeters and has a micro-pore size range of 0.1 to 30 microns, 0.1 to 20 microns, 0.1 to 10 microns or 0.1 to 5 microns. The porosity of bone substitute material is 50 to 95%.

According to a further aspect of the present invention, the method of the invention further comprises a step of attaching polymers or bioactive agents to the pores of the bone substitute material by the method of coating, insertion or addition. According to the invention, the agent is selected from the group consisting of demineralized bone matrix, growth factors, bone morphogenic proteins, antibiotic agents, vitamin, collagen, mesenchymal stem cells, antitumor agents, cellular attachment agents, immunosuppressant, clot activator and platelet-rich fibrin gel, and silk protein.

Figure 7:
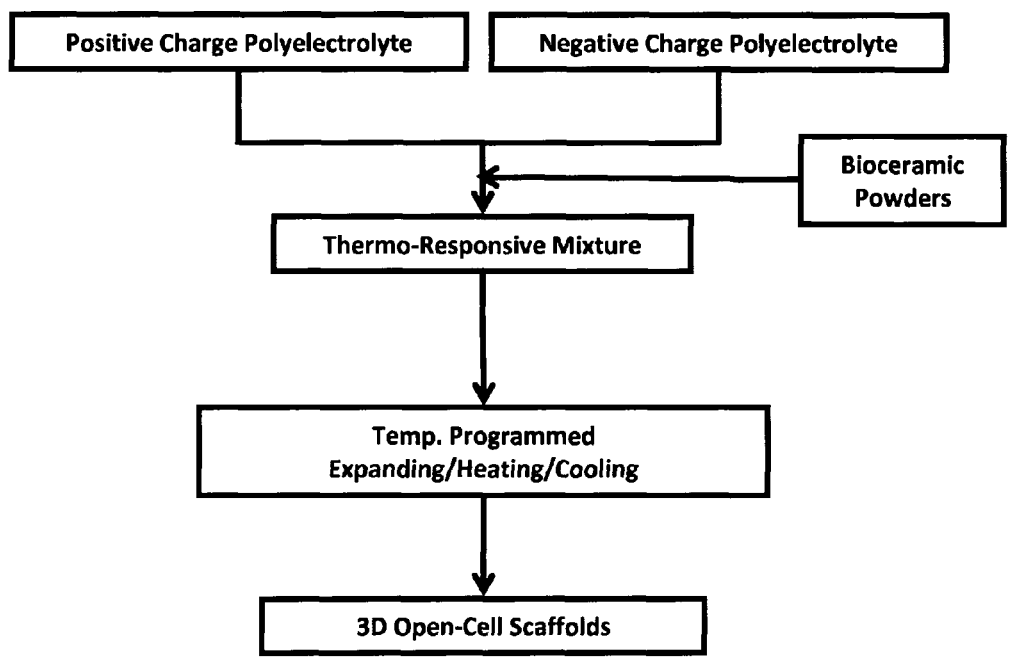
FIG. 7 illustrates the flow chart of the method of the invention using a heat responsive mixture to form an inorganic interconnected 3D open-pore bone substitute.

The method of the invention can be exemplified by FIG. 7.

The method of the invention does not require any pore formation agents or molds. The method only requires mixing bioceramics in a polyelectrolyte complex to form a heat responsive mixture. Preferably, the mixture is in the form of a gel. A three-dimensional (3D) network structure is formed after heating the resulting mixture of the polyelectrolyte complex and the bioceramic through a physical crosslinking mechanism, which is formed by the attraction of physical columbic forces between two oppositely-charged polyelectrolytes in aqueous solution.

During heating, control of the swelling ratio of mixture, evaporation rate of water, and the gasified rate of the polymer colloid are exercised to form different pore sizes, porosity, and interconnectivity of pore structure. By selecting suitable inorganic materials, and controlling sintering conditions, bone substitutes of different compositions, physical properties or degree of crystallization can be prepared. The various bone regeneration rates needed for particular clinical applications and different parts of bones that can be achieved by adjusting ceramic composition and physical properties of the bone substitute. In addition, the polyelectrolyte complex functions as a binder, which can significantly enhance the mechanical integrity of the ceramic sample after sintering. The invention provides a large block bone substitute having 3D interconnected micropores and micropores which can facilitate improved bone regeneration.

EXAMPLES

Example 1

Expansion of Heat Responsive Mixture of the Invention

The positive charge polyelectrolyte (10% Chitosan) solution and negative charge polyelectrolyte (2% HPMC) solution were mixed to form a polyelectrolytic complex, and the biomedical ceramic powders (HA:β-TCP=1:9) were then added to the complex to form a mixture by using a mixer, the weight percent of PEC, biomedical ceramic powder, and water is 6%, 25%, and 69%, respectively, in system. The volume of the mixture expanded from a temperature of around 55° C. After heating the resulting mixture to 75° C., the volume of the mixture expanded to 3.3 times the volume of the mixture at 25° C. (FIG. 1, (C) and (D)).

Comparative Example 1

Expansion of Polyelectrolyte Complex

The positive charge polyelectrolyte (10% Chitosan) solution and negative charge polyelectrolyte (2% HPMC) solutions were mixed to form a polyelectrolytic complex. After heating the complex to 75° C., its volume was not significantly changed in comparison with that of the complex at 25° C. (FIG. 1, (A) and (B)).

Example 2

Production of 3D Open-Cell Bone Substitutes

The positive charge polyelectrolyte (Chitosan) and negative charge polyelectrolyte (HPMC) were mixed at a ratio of 1:1 (w/w, dry weight) and then a biomedical ceramic powder was added for mixing by using a mixer. The weight percent of PEC, biomedical ceramic powder, and water is 6%, 25%, and 69%, respectively, in system. The mixed material was put in the zirconia crucible, which was placed in a high temperature oven to raise its temperature in several stages. The heating process can be divided into three stages. In the first stage the temperature was raised from room temperature to 100° C. and then held for 1 hour. The heat for the second stage was raised from 100 to 300° C. at a rate of 1.67° C./min, held for 1 hour at 300° C., and then raised from 300 to 1150° C. at a rate of 3.5° C./min for the third stage and held for 5 hours at 1150° C. After sintering, the product was cooled in the oven.

Figure 2:
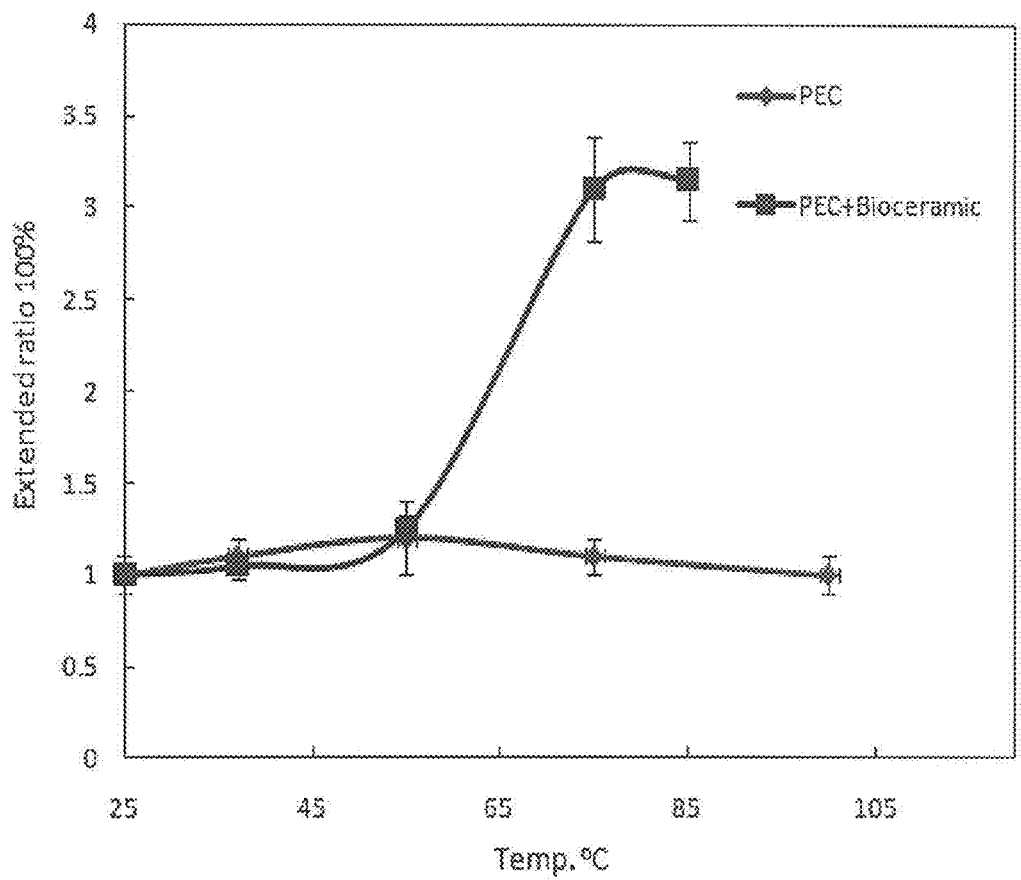
FIG. 2 shows the relationship between the volume and temperature of a chitosan/HPMC polyelectrolytic complex (Comparative Example 1) and a heat-responsive mixture of a chitosan/HPMC polyelectrolytic complex and biomedical ceramic powders (HA:β-TCP=1:9) (Example 1).
Figure 3:
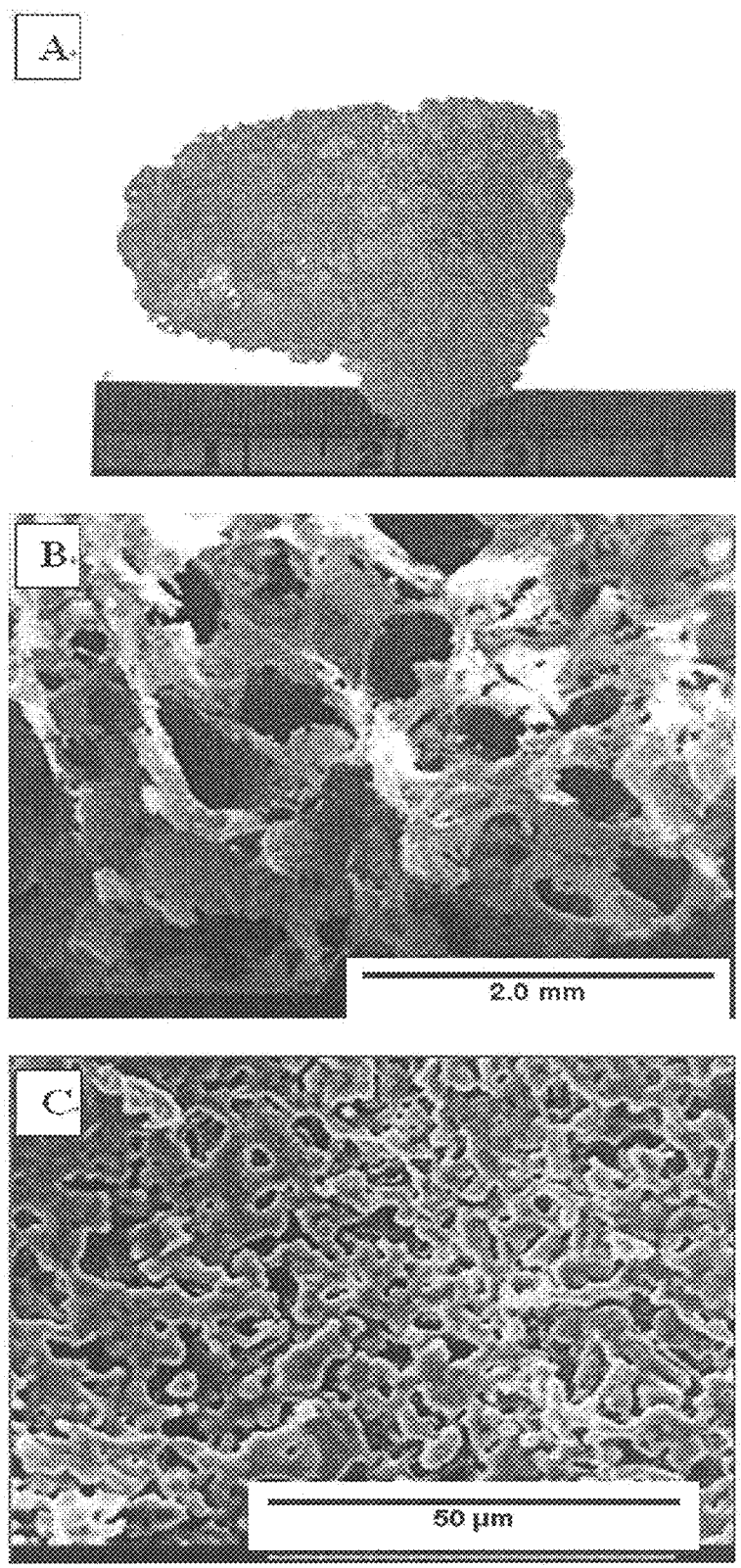
FIG. 3 shows the porous structure of the bone substitute material of the present invention observed by SEM (Example 2); wherein (A) refers to optical micrograph of specimen; (B) refers to SEM micrograph of specimen (20×); and (C) refers to SEM micrograph of specimen (1,000×).

FIG. 2 shows the relationship between the volume and temperature of a chitosan/HPMC polyelectrolytic complex (Comparative Example 1) and a heat-responsive mixture of a chitosan/HPMC polyelectrolytic complex and biomedical ceramic powder. The porous structure of the resulting product is observed with SEM as shown in FIG. 3. Using image processing software of ImageJ 1.37c (National Institutes of Health (NIH), Bethesda, Md., USA; freeware from http://rsb.info.nih.gov/ij) to calculate the pore size, we can achieve a micro-pore size of 9±7 μm, and the macro-pore size of 431±220 μm with porosity of 91.9%.

Examples 2 to 12 and Comparative Data between Examples 2 to 12 and Comparative Examples With steps similar to those of Example 2, other examples can be obtained. The parameters of the preferred examples and the comparative example are listed in Tables 2 to 6.

From Table 2, it is shown that all the examples have better porous structure than the comparative Examples. Holding other parameters the same, the data showed that using both a positive charge polyelectrolyte and a negative charge polyelectrolyte in low amounts could result in the porous structure formation. The porous structure could not be observed when only positive charge polyelectrolyte or only negative charge polyelectrolyte was used in the comparative examples 2 to 4. In addition, the size of the pores can be altered by using different negative charge polyelectrolyte in the Examples 2 to 5.

TABLE 2

| | | Example 2 | Example 3 | Example 4 | Example 5 | Comparative Example 2 | Comparative Example 3 | Comparative Example 4 |
|---|---|---|---|---|---|---|---|---|
| Materials | Positive charge polyelectrolyte (wt %) | Chitosan 10 | Chitosan 10 | Chitosan 10 | Chitosan 10 | Chitosan 10 | — | — |
| | Negative charge polyelectrolyte (wt %) | HPMC 2 | γ-PGA 2 | CMC 2 | Alginate 2 | — | HPMC 2 | — |
| | Bioceramic based compound (wt ratio) | β-TCP:HA (9:1) | β-TCP:HA (9:1) | β-TCP:HA (9:1) | β-TCP:HA (9:1) | β-TCP:HA (9:1) | β-TCP:HA (9:1) | β-TCP:HA (9:1) |
| | Composition of mixture (PEC or polymer, bioceramic, and water) (wt %) | 6%, 25%, 69% | 6%, 25%, 69% | 6%, 25%, 69% | 6%, 25%, 69% | 3%, 25%, 72% | 3%, 25%, 72% | |
| | Porogen | none | none | none | none | none | none | NaCl (50%) |
| First heating stage | Heating rate from 25-100° C. (° C./min) | 1.67 | 1.67 | 1.67 | 1.67 | 1.67 | 1.67 | 1.67 |
| | Holding time (hr) | 1 | 1 | 1 | 1 | 1 | 1 | 1 |
| Second heating stage | Heating rate from 100 to 300° C. (° C./min) | 1.67 | 1.67 | 1.67 | 1.67 | 1.67 | 1.67 | 1.67 |
| | Holding time at 300° C. (hr) | 1 | 1 | 1 | 1 | 1 | 1 | 1 |
| Third heating stage | Heating rate from 300 to 1,150° C. (° C./min) | 3.5 | 3.5 | 3.5 | 3.5 | 3.5 | 3.5 | 3.5 |
| | Holding time at 1,150° C. (hr) | 5 | 5 | 5 | 5 | 5 | 5 | 5 |
| Structure | Macro-pore (μm) | 431 ± 220 | 1,538 ± 634 | 1,151±661 | 552±146 | N.D. | N.D. | N.D. |
| | Micro-pore (μm) | 9 ± 7 | 15 ± 10 | 9 ± 8 | 30 ± 20 | N.D. | N.D. | N.D. |

Figure 4:
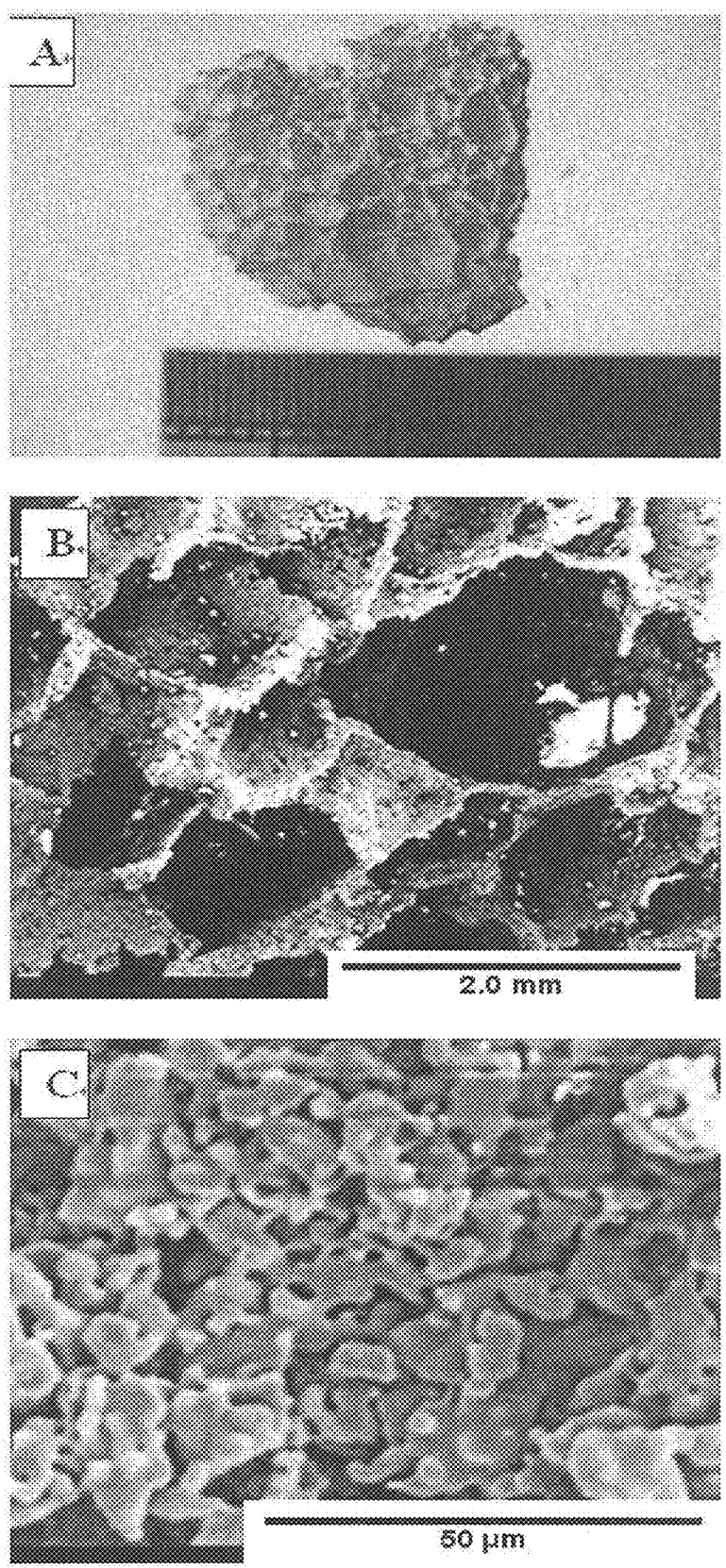
FIG. 4 shows the porous structure of the bone substitute material of the present invention observed by SEM (Example 6); wherein (A) refers to optical micrograph of specimen; (B) refers to SEM micrograph of specimen (20×) and (C) refers to SEM micrograph of specimen (1,000×).
Figure 5:
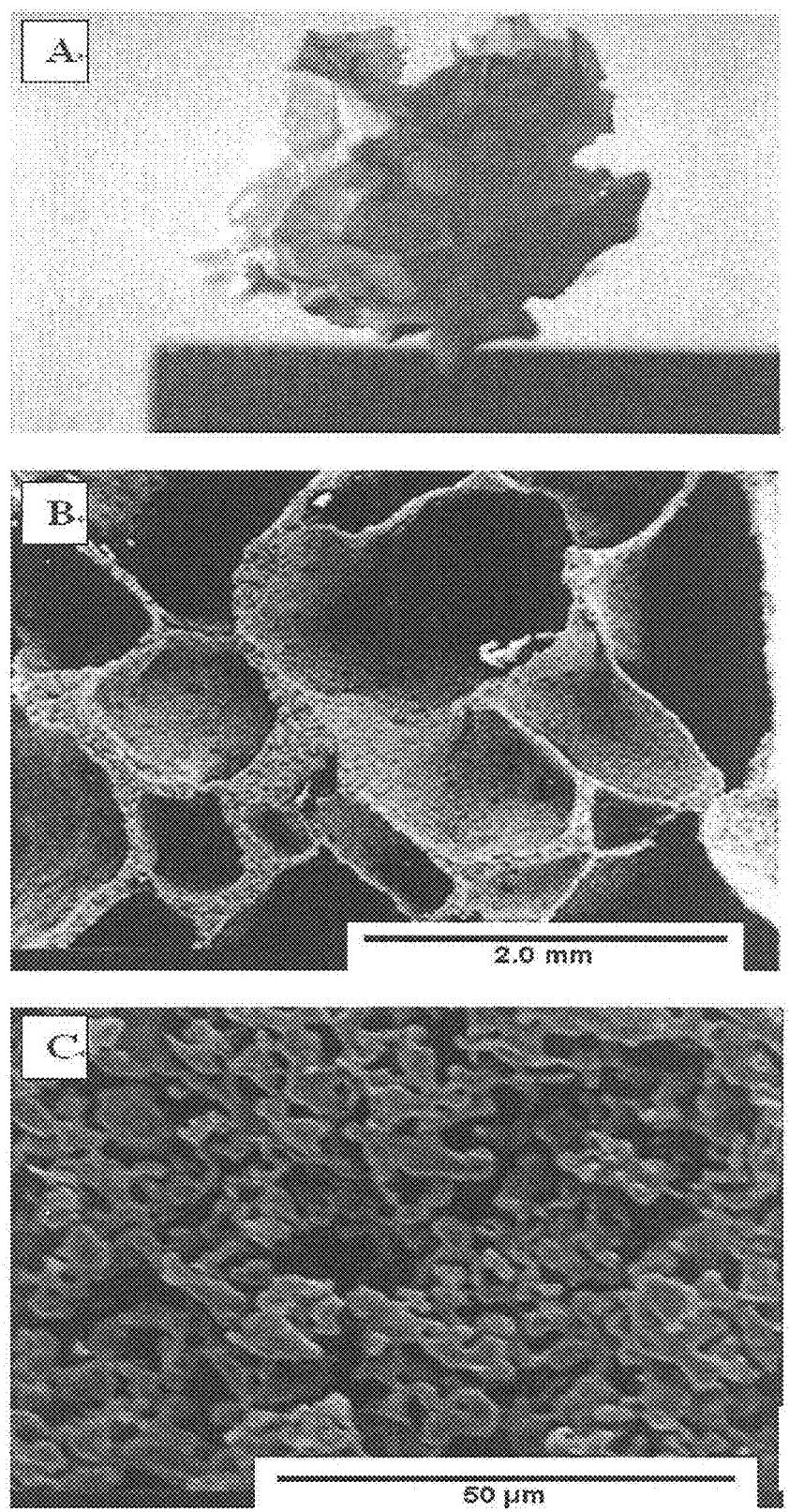
FIG. 5 shows the porous structure of the bone substitute material of the present invention observed by SEM (Example 7); wherein (A) refers to optical micrograph of specimen; (B) refers to SEM micrograph of specimen (20×) and (C) refers to SEM micrograph of specimen (1,000×).

From Table 3, it is shown that the porous structure can be controlled with the heating rate of the heating process. Holding other parameters the same, the size of pores increases with the decrease of the heating rate in the pore-forming condition. The SEM photographs of Example 6 and 7 were shown in FIGS. 4 and 5, respectively.

TABLE 3

| | | Example 2 | Example 6 | Example 7 |
|---|---|---|---|---|
| Materials | (A) Positive charge polyelectrolyte (wt %) | Chitosan 10 | Chitosan 10 | Chitosan 10 |
| | (B) Negative charge polyelectrolyte (wt %) | HPMC 2 | HPMC 2 | HPMC 2 |
| | (C) Bioceramic based compound (wt ratio) | β-TCP:HA (9:1) | β-TCP:HA (9:1) | β-TCP:HA (9:1) |
| | Composition of mixture (PEC, bioceramic, and water) (wt %) | 6%, 25%, 69% | 6%, 25%, 69% | 6%, 25%, 69% |
| | Porogen | none | none | None |
| First heating stage | Heating rate from 25-100° C. (° C./min) | 1.67 | 0.63 | 0.42 |

TABLE 3-continued

|  |  | Example 2 | Example 6 | Example 7 |
|---|---|---|---|---|
|  | Holding time (hr) | 1 | 1 | 1 |
| Second heating stage | Heating rate from 100 to 300° C. (° C./min) | 1.67 | 1.67 | 1.67 |
|  | Holding time at 300° C. (hr) | 1 | 1 | 1 |
| Third heating stage | Heating rate from 300 to 1,150° C. (° C./min) | 3.5 | 3.5 | 3.5 |
|  | Holding section at 1,150° C. (hr) | 5 | 5 | 5 |
| Structure | Macro-pore (μm) | 431 ± 220 | 1,033 ± 278 | 2,320 ± 778 |
|  | Micro-pore (μm) | 9 ± 7 | 9 ± 7 | 14 ± 13 |

Figure 6:
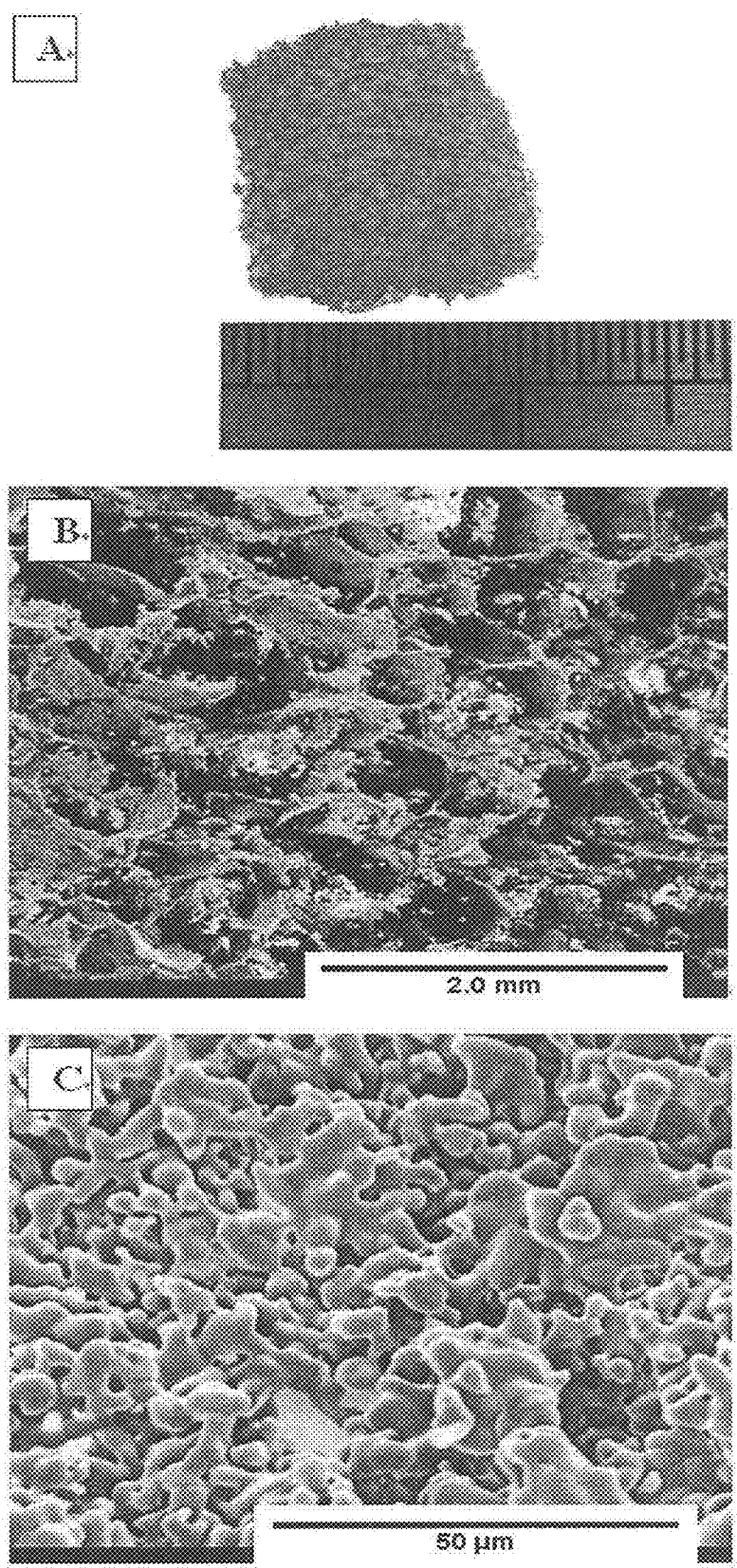
FIG. 6 shows the porous structure of the bone substitute material of the present invention observed by SEM (Example 9); wherein (A) refers to optical micrograph of specimen; (B) refers to SEM micrograph of specimen (20×) and (C) refers to SEM micrograph of specimen (1,000×).

Table 4 shows that the porous structure is affected by the concentration of the positive and negative charge polyelectrolyte. In Example 8, with chitosan 15% and HPMC 3% the final product has the size of macro-pore 514±178 μm and the size of micro-pore 7±4 μm. In Example 8, with chitosan 20% and HPMC 4% the final product has the size of macro-pore 367±117 μm and the size of micro-pore 6±4 μm. In addition, the size of the pores can be altered by using different negative charge polyelectrolyte in the Examples 2, 8, and 9. The SEM photographs of Examples 9 were shown in FIG. 6.

TABLE 4

|  |  | Example 2 | Example 8 | Example 9 |
|---|---|---|---|---|
| Materials | (A) Positive charge polyelectrolyte (wt %) | Chitosan 10 | Chitosan 15 | Chitosan 20 |
|  | (B) Negative charge polyelectrolyte (wt %) | HPMC 2 | HPMC 3 | HPMC 4 |
|  | (C) Bioceramic based compound (wt ratio) | β-TCP:HA (9:1) | β-TCP:HA (9:1) | β-TCP:HA (9:1) |
|  | Composition of mixture (PEC, bioceramic, and water) (wt %) | 6%, 25%, 69% | 9%, 25%, 66% | 12%, 25%, 63% |
|  | Porogen | none | none | none |
| First heating stage | Heating rate from 25-100° C. (° C./min) | 1.67 | 1.67 | 1.67 |
|  | Holding time (hr) | 1 | 1 | 1 |
| Second heating stage | Heating rate from 100 to 300° C. (° C./min) | 1.67 | 1.67 | 1.67 |
|  | Holding section at 300° C. (hr) | 1 | 1 | 1 |
| Third heating stage | Heating rate from 300 to 1,150° C. (° C./min) | 3.5 | 3.5 | 3.5 |
|  | Holding time at 1,150° C. (hr) | 5 | 5 | 5 |
| Structure | Macro-pore (μm) | 431 ± 220 | 514 ± 178 | 367 ± 117 |
|  | Micro-pore (μm) | 9 ± 7 | 7 ± 4 | 6 ± 4 |

Table 5 shows that the porous structure is affected by the ratio of the calcium-phosphate based compound. In Example 9, the amount of ceramic material was increased so that the ratio was 1:1:0.93 and the product thereof has the size of macro-pore 390±314 μm and the size of micro-pore 10±9 μm.

TABLE 5

|  |  | Example 2 | Example 10 |
|---|---|---|---|
| Materials | (A) Positive charge polyelectrolyte (wt %) | Chitosan 10 | Chitosan 10 |
|  | (B) Negative charge polyelectrolyte (wt %) | HPMC 2 | HPMC 2 |
|  | (C) Bioceramic based compound (wt ratio) | β-TCP:HA (9:1) | β-TCP:HA (9:1) |
|  | Composition of mixture (PEC, bioceramic, and water) (wt %) | 6%. 25%, 69% | 6%, 32%, 62% |
| First heating stage | Heating rate from 25-100° C. (° C./min) | 1.67 | 1.67 |
|  | Holding time (hr) | 1 | 1 |
| Second heating stage | Heating rate from 100 to 300° C. (° C./min) | 1.67 | 1.67 |
|  | Holding time at 300° C. (hr) | 1 | 1 |
| Third heating stage | Heating rate from 300 to 1,150° C. (° C./min) | 3.5 | 3.5 |
|  | Holding time at 1150° C. (hr) | 5 | 5 |
| Structure | Macro-pore (μm) | 431 ± 220 | 390 ± 314 |
|  | Micro-pore (μm) | 9 ± 7 | 10 ± 9 |

Table 6 shows that the porous specimens were produced with various ceramic compositions. For example, β-TCP and CaSO$_4$ were used in Example 10 and final product thereof has the size of macro-pore 656±407 μm and the size of micro-pore 13±18 μm. Moreover, ZrO$_2$ was used as ceramic material in Example 12 and thereof has the size of macro-pore 285±259 μm.

TABLE 6

|  |  | Example 9 | Example 11 | Example 12 |
|---|---|---|---|---|
| Materials | (A) Positive charge polyelectrolyte (wt %) | Chitosan 20 | Chitosan 20 | Chitosan 20 |

TABLE 6-continued

|  |  | Example 9 | Example 11 | Example 12 |
|---|---|---|---|---|
|  | (B) Negative charge polyelectrolyte (wt %) | HPMC 4 | HPMC 4 | HPMC 4 |
|  | (C) Bioceramic based compound (wt ratio) | β-TCP:HA (9:1) | β-TCP:CaSO$_4$ (1:1) | ZrO$_2$ |
|  | Composition of mixture (PEC, bioceramic, and water) (wt %) | 12%, 25%, 63% | 12%, 25%, 63% | 12%, 25%, 63% |
| First heating stage | Heating rate from 25-100° C. (° C./min) | 1.67 | 1.67 | 1.67 |
|  | Holding time (hr) | 1 | 1 | 1 |
| Second heating stage | Heating rate from 100 to 300° C. (° C./min) | 1.67 | 1.67 | 1.67 |
|  | Holding time at 300° C. (hr) | 1 | 1 | 1 |
| Third heating stage | Heating rate (° C./min) | 3.5 (300-1,150° C.) | 3.5 (300-1,150° C.) | 3.5 (300-1,400° C.) |
|  | Holding section (° C.) | 1,150 (5 hr) | 1,150 (5 hr) | 1,400 (5 hr) |
| Structure | Macro-pore (μm) | 367 ± 117 | 656 ± 407 | 285 ± 259 |
|  | Micro-pore (μm) | 6 ± 4 | 13 ± 12 | N.D. |

The invention is not limited by the embodiments described above which are presented as examples only but can be modified in various ways within the scope of protection defined by the appended patent claims.

What is claimed is:

1. A method of using a heat responsive mixture to form an inorganic interconnected 3D open-pore bone substitute, wherein the heat responsive mixture comprises one or more polyelectrolytic complexes and one or more biomedical ceramic powders, comprising a first heating step of heating the mixture at a temperature ranging from 25° C. to 100° C., a second heating step of heating the resulting mixture to remove water and polyelectrolytic complexes contained therein and then cooling the mixture, resulting in an inorganic interconnected 3D open-pore bone substitute;
   wherein after raising the temperature at the first heating step or the second heating step can further comprises a temperature-holding session for 0.25 to 10 hours;
   wherein the polyelectrolytic complex is a gel form and formed by one or more positive charge polyelectrolyte and one or more negative charge polyelectrolyte;
   wherein the positive charge polyelectrolyte is selected from the group consisting of polyarginine, polyornithine, DEAE dextran, polybrene, chitosan, polylysine, amino-cellulose, polyethyleneimine resin and mixture thereof and the negative charge polyelectrolyte is selected from the group consisting of: acetylcellulose, γ-polyglutamate (γ-PGA), hydroxypropyl methyl cellulose (HPMC), carboxy methyl cellulose (CMC), sodium polyphosphate, hyaluronan acid, sodium alginate and mixture thereof;
   wherein the biomedical ceramic powder is selected from the group consisting of: calcium phosphate based ceramic powder, calcium sulfate based ceramic powder, oxide based ceramic powder, nitride based ceramic powder, carbide based ceramic powder, alumina-dispersed zirconia, titania-dispersed alumina and mixture thereof; and
   wherein the weight percent (w/w, dry weight) of a polyelectrolyte complex and a biomedical ceramic material ranges from 2% to 20% and 15% to 50%, respectively, the remained composition is water.

2. The method according to claim 1 wherein the calcium phosphate based ceramic powder is selected from the group consisting of hydroxyapatite (HA), β-tricalcium phosphate (β-TCP), amorphous calcium phosphate (ACP) and mixture thereof.

3. The method according to claim 1 wherein the calcium sulfate based ceramic powder is selected from the group consisting of calcium sulfate dihydrate, calcium sulfate hemihydrate, and calcium sulfate anhydrate.

4. The method according to claim 1 wherein oxide ceramic based powder is selected from the group consisting of alumina, zirconia and titania.

5. The method according to claim 1 wherein the nitride based ceramic powder is selected from the group consisting of silicon nitride, titanium nitride and aluminum nitride.

6. The method according to claim 1 wherein the carbide based ceramic powder is silicon carbide.

7. The method according to claim 1, wherein the temperature for heating the heat responsive mixture ranges from 55° C. to 100° C.

8. The method according to claim 1, wherein the temperature used in the second heating step is from 85° C. to 1500° C. and the heating can be completed with more than one stage.

9. The method according to claim 1, wherein the temperatures used in the second heating step are from 100° C. to 250° C., and then from 300° C. to 1300° C.

10. The method according to claim 1, wherein the first heating step and the second heating step can be completed with more than one stage.

11. The method according to claim 1, wherein the heating rate in the first heating step is 0.1 to 20° C./min.

12. The method according to claim 1, the temperature-holding session is 1 to 8 hours.

13. The method according to claim 1, wherein the bone substitute material has a macro-pore size range of 0.05 millimeter to 5 millimeter.

14. The method according to claim 1, wherein the porosity of the bone substitute material is 50 to 95%.

15. The method according to claim 1, which further comprises a step of attaching a polymer or a bioactive agent to the pores of the bone substitute material.

16. The method according to claim 15, wherein the agent is selected from the group consisting of demineralized bone matrix, growth factors, bone morphogenic proteins, antibiotic agents, vitamin, collagen, mesenchymal stem cells, antitumor agents, cellular attachment agents, immunosuppressant, clot activators and platelet-rich fibrin gel, and silk proteins.

* * * * *